(12) United States Patent  
Hughes

(10) Patent No.: US 8,952,787 B2  
(45) Date of Patent: Feb. 10, 2015

(54) LABORATORY SAMPLE ARCHIVING APPARATUS AND METHOD

(76) Inventor: Thomas Fergus Hughes, East Sussex (GB)

( * ) Notice: Subject to any disclaimer, the term of this patent is extended or adjusted under 35 U.S.C. 154(b) by 558 days.

(21) Appl. No.: 13/003,225

(22) PCT Filed: Jul. 9, 2009

(86) PCT No.: PCT/GB2009/050810  
§ 371 (c)(1),  
(2), (4) Date: Jan. 7, 2011

(87) PCT Pub. No.: WO2010/004331  
PCT Pub. Date: Jan. 14, 2010

(65) Prior Publication Data  
US 2011/0115610 A1    May 19, 2011

(30) Foreign Application Priority Data  
Jul. 9, 2008    (GB) .................................. 0812540.3

(51) Int. Cl.  
*H04Q 5/22*    (2006.01)  
*B01L 9/00*    (2006.01)  
(Continued)

(52) U.S. Cl.  
CPC ............ *B01L 9/00* (2013.01); *G01N 35/00732* (2013.01); *G06K 17/0006* (2013.01);  
(Continued)

(58) Field of Classification Search  
USPC ................. 340/10.1–10.6, 572.1–572.9, 235; 235/375–385  
See application file for complete search history.

(56) References Cited

U.S. PATENT DOCUMENTS 4,636,634 A * 1/1987 Harper et al. ............. 250/223 R  
5,287,414 A * 2/1994 Foster .......................... 382/100  
(Continued)

FOREIGN PATENT DOCUMENTS

JP    2008-218051    8/2006  
WO    WO 00/16280    3/2000  
(Continued)

OTHER PUBLICATIONS

UK Search Report under Section 17 for GB0812540.3 (dated Nov. 5, 2008).

(Continued)

*Primary Examiner* — George Bugg  
*Assistant Examiner* — Paul Obiniyi  
(74) *Attorney, Agent, or Firm* — Fay Sharpe LLP

(57) ABSTRACT

An archive apparatus is provided for storing and archiving laboratory samples including radio frequency identification means. The apparatus comprises a support structure or cabinet (4), a drawer (6) translatable in a translation direction (12) into and out of the support structure (4), and sample support means comprising ribs (8) associated with the drawer (6) for supporting an array (10) of samples or slides (20) spaced along the translation direction (12) for movement with the drawer (6). A radio frequency reader antenna (14) is connected to the support structure (4) adjacent to the drawer (6) and recording means (34, 38) are adapted to operatively communicate with the reader antenna (14) to store information obtained from the radio frequency identification means of laboratory samples or slides (20) supported by the drawer (6). The apparatus can automatically collect and store current information concerning the samples or slides (20) in the drawer (6) as a consequence of opening and closing of the drawer (6).

13 Claims, 3 Drawing Sheets

(51) Int. Cl.
*G01N 35/00* (2006.01)
*G06K 17/00* (2006.01)
*G01N 35/04* (2006.01)

(52) U.S. Cl.
CPC ....... G06K17/0022 (2013.01); *B01L 2300/022* (2013.01); *G01N 2035/0498* (2013.01); *G06K 2017/0051* (2013.01); *G06K 2017/0074* (2013.01)
USPC ..... 340/10.1; 340/10.2; 340/10.3; 340/10.31; 340/10.32; 340/10.4; 340/10.41; 340/10.42; 340/10.5; 340/10.51; 340/10.52; 340/10.6; 235/375; 235/376; 235/377; 235/378; 235/379; 235/380; 235/381; 235/382; 235/382.5; 235/383; 235/384; 235/385

(56) References Cited

U.S. PATENT DOCUMENTS

| | | | | |
|---|---|---|---|---|
| 5,455,409 A * | 10/1995 | Smith et al. | | 235/385 |
| 5,676,439 A * | 10/1997 | Occhipinti et al. | | 312/183 |
| 5,721,531 A * | 2/1998 | Garver et al. | | 340/8.1 |
| 5,739,765 A * | 4/1998 | Stanfield et al. | | 340/8.1 |
| 5,751,221 A * | 5/1998 | Stanfield et al. | | 340/5.74 |
| 5,805,075 A * | 9/1998 | Carlson et al. | | 312/215 |
| 5,918,955 A * | 7/1999 | Graham | | 312/193 |
| 5,977,875 A * | 11/1999 | Lin et al. | | 340/570 |
| 6,204,764 B1 * | 3/2001 | Maloney | | 340/568.1 |
| 6,407,665 B2 * | 6/2002 | Maloney | | 340/568.1 |
| 6,867,695 B2 * | 3/2005 | Prado et al. | | 340/568.1 |
| 6,933,849 B2 * | 8/2005 | Sawyer | | 340/572.4 |
| 7,079,044 B1 * | 7/2006 | Stanfield et al. | | 340/8.1 |
| 7,202,785 B2 * | 4/2007 | Maloney | | 340/568.1 |
| 7,268,687 B2 * | 9/2007 | Egbert et al. | | 340/572.7 |
| 7,274,285 B2 * | 9/2007 | Chaloner et al. | | 340/10.4 |
| 7,301,470 B2 * | 11/2007 | Stanfield et al. | | 340/8.1 |
| 7,317,393 B2 * | 1/2008 | Maloney | | 340/568.1 |
| 7,511,601 B2 * | 3/2009 | Eisenberg et al. | | 340/3.51 |
| 7,518,516 B2 * | 4/2009 | Azevedo et al. | | 340/572.1 |
| 7,551,089 B2 * | 6/2009 | Sawyer | | 340/572.4 |
| 7,623,032 B2 * | 11/2009 | Niederland et al. | | 340/568.1 |
| 7,644,017 B2 * | 1/2010 | Pippia et al. | | 705/28 |
| 7,668,620 B2 * | 2/2010 | Shoenfeld | | 700/237 |
| 7,689,460 B2 * | 3/2010 | Natori et al. | | 705/22 |
| 7,734,372 B2 * | 6/2010 | Shoenfeld | | 700/237 |
| 7,791,479 B2 * | 9/2010 | Dearing et al. | | 340/572.1 |
| 7,808,367 B2 * | 10/2010 | Moore | | 340/10.3 |
| 7,834,765 B2 * | 11/2010 | Sawyer | | 340/572.4 |
| 7,834,766 B2 * | 11/2010 | Sawyer | | 340/572.4 |
| 7,994,897 B2 * | 8/2011 | Azevedo et al. | | 340/5.73 |
| 8,095,435 B2 * | 1/2012 | Newton et al. | | 705/28 |
| 8,140,187 B2 * | 3/2012 | Campbell et al. | | 700/242 |
| 8,231,053 B2 * | 7/2012 | Linton et al. | | 235/382 |
| 2001/0006368 A1 * | 7/2001 | Maloney | | 340/568.1 |
| 2002/0014961 A1 * | 2/2002 | Maloney | | 340/568.1 |
| 2002/0145520 A1 * | 10/2002 | Maloney | | 340/568.1 |
| 2004/0008114 A1 * | 1/2004 | Sawyer | | 340/572.1 |
| 2004/0095241 A1 * | 5/2004 | Maloney | | 340/568.1 |
| 2005/0156739 A1 * | 7/2005 | Maloney | | 340/572.1 |
| 2005/0205670 A1 * | 9/2005 | Natori et al. | | 235/383 |
| 2006/0022827 A1 | 2/2006 | Higham | | |
| 2006/0079994 A1 * | 4/2006 | Chu et al. | | 700/231 |
| 2007/0023518 A1 * | 2/2007 | Tada et al. | | 235/435 |
| 2007/0244598 A1 * | 10/2007 | Shoenfeld | | 700/236 |
| 2008/0094214 A1 * | 4/2008 | Azevedo et al. | | 340/568.1 |
| 2008/0122615 A1 * | 5/2008 | Shoenfeld | | 340/540 |
| 2009/0189767 A1 * | 7/2009 | Primm et al. | | 340/572.1 |
| 2009/0251293 A1 * | 10/2009 | Azevedo et al. | | 340/10.1 |
| 2009/0278686 A1 * | 11/2009 | Sawyer | | 340/572.1 |
| 2009/0295582 A1 * | 12/2009 | Sawyer | | 340/572.1 |
| 2010/0106291 A1 * | 4/2010 | Campbell et al. | | 700/231 |
| 2010/0187306 A1 * | 7/2010 | Solomon | | 235/385 |
| 2010/0289620 A1 * | 11/2010 | Aminger et al. | | 340/10.1 |
| 2011/0025503 A1 * | 2/2011 | Weaver | | 340/572.1 |
| 2011/0068169 A1 * | 3/2011 | Ross et al. | | 235/379 |
| 2011/0133905 A1 * | 6/2011 | Hussain et al. | | 340/10.42 |
| 2012/0019358 A1 * | 1/2012 | Azevedo et al. | | 340/5.65 |

FOREIGN PATENT DOCUMENTS

| | | |
|---|---|---|
| WO | WO 2004/006051 A2 | 1/2004 |
| WO | WO 2007/0058048 A1 | 5/2007 |
| WO | WO 2007/112413 A2 | 10/2007 |

OTHER PUBLICATIONS

International Search Report for PCT/GB2009/050810 (mailing date Oct. 30, 2009).

* cited by examiner

LABORATORY SAMPLE ARCHIVING APPARATUS AND METHOD

This application claims the benefit of PCT International Patent Application No. PCT/GB2009/050810, filed on 9 Jul. 2009, and claims the benefit of UK Patent Application GB0812540.3, filed on Jul. 9, 2008, the disclosures of which are incorporated herein by reference.

The present invention relates to an apparatus and a method for archiving laboratory samples.

Laboratory samples are customarily stored by being mounted on slides or accommodated in so-called cassettes or other receptacles. For simplicity, reference below has simply been made to slides. The slides are customarily accommodated drawers which are translatable in and out of cabinets holding plural rows and columns of drawers. A laboratory may keep thousands of slides and need to maintain a record of the whereabouts of the sides for many years during which the slides may be taken in and out of the cabinets. Maintaining accurate records concerning which slides are in the cabinets at any one time and when they were taken in and out of the cabinets is a time consuming task and prone to human error. If a conventional radio frequency identification (RFID) reader is used to assist in the archiving process the closeness of the slides to each other in a typical laboratory cabinet drawer causes problems with an RFID signal from one slide being masked or shadowed by radio RFID tags of adjacent slides. The conventional reader may also pick-up signals from RFID tags of adjacent slides which it is not intended to pick-up.

An object of the invention is to provide an archiving apparatus and method which at least partly overcome the problems referred to above.

Thus according to the invention there is provided an archive apparatus for storing and archiving laboratory samples including radio frequency identification means the apparatus comprising a support structure, a drawer translatable in a translation direction into and out of the support structure, sample support means associated with the drawer for supporting an array of samples spaced along the translation direction for movement with the drawer, a radio frequency reader antenna connected to the support structure adjacent to the drawer and recording means adapted to operatively communicate with the reader antenna to store information obtained from the radio frequency identification means of laboratory samples supported by the drawer. With such an apparatus, because the reader antenna is connected to the support structure adjacent to the drawer it can be positioned in an optimum manner relative to samples or slides to eliminate the problem of masking referred to above. Furthermore the operative communication between the reader antenna and the recording means permits the information from the radio frequency identification means to be stored by the recording means without human intervention thus cutting out human error and the significant time involved in prior art archiving systems. The drawer can enable the samples to be orientated so that they can be read easily by the reader antenna.

The reader antenna is preferably configured to emit a curtain of electromagnetic waves. With such an arrangement the reader antenna can be arranged to communicate with the radio frequency identification means associated with a limited number of slides or samples. If RFID tags of the slides are so-called passive RFID tags then they will only emit a signal upon receipt of a signal from the reader antenna.

More preferably the curtain of electromagnetic waves and the sample support means are configured such that the curtain of electromagnetic waves interacts with the radio frequency identification means of a limited number of laboratory samples at any one time as the drawer is translated in the translation direction. Most preferably this number is limited to one.

Preferably the recording means includes a control means operatively connected to the reader antenna and a single control means may advantageously be operatively connected to plural reader antennae connected to the same support structure.

In order to provide a system which can automatically track movements of slides into and out of the support structure preferably the control means is operatively connected to a computer system including sample tracking software. The tracking software may comprise software such as the tracking software marketed under the name LambTrack.

Since laboratories often accommodate many drawers of slides, preferably the support structure accommodates plural drawers and more preferably one said reader antenna is connected to the support structure adjacent to each drawer.

When the support structure accommodates plural drawers each with an associated reader antenna the control means is preferably operatively connected to plural said reader antennae.

The apparatus may not be limited to a single support structure and may advantageously comprise a compound archive apparatus including plural archive apparatuses as described above. In such a compound archive apparatus the recording means preferably includes a single computer system operatively connected to the reader antennae. In this manner a single system can be used to track the movements of slides into and out of all support structures in a given laboratory or possibly in several laboratories between which the slides may be transferred for various operations.

According to a second aspect of the invention there is provided a method for storing and archiving laboratory samples with radio frequency identification means including providing apparatus comprising a support structure, a drawer translatable in a translation direction into and out of the support structure, supporting the laboratory samples in an array in sample support means associated with the drawer with the laboratory samples spaced along the translation direction for movement with the drawer, providing a radio frequency reader antenna connected to the support structure adjacent to the drawer and recording means, translating the drawer in the translation direction so that the laboratory samples pass the reader antenna, operatively communicating information from the radio frequency identification means of the samples supported by the drawer to the recording means and recording said information with the recording means.

The method preferably also comprises the further steps of at least partly translating the drawer out of the support structure, altering a distribution of the samples supported by the drawer, translating the drawer back into the support structure and updating a record held by the recording means of samples supported by the drawer based on signals received by the reader antenna.

In order that the method not only records information concerning the slides currently in the drawer the method preferably also records historic information concerning the samples in the drawer in addition to current information concerning the samples in the drawer.

To assist in the interpretation of the information held by the recording means, preferably the stored information concerning samples supported by the drawer is displayed by the recording means graphically. Alternatively the information could be displayed as text or as a combination of text and graphic representations.

The invention will now be described by way of example only with reference to the accompanying schematic drawings in which.

Figure 1:
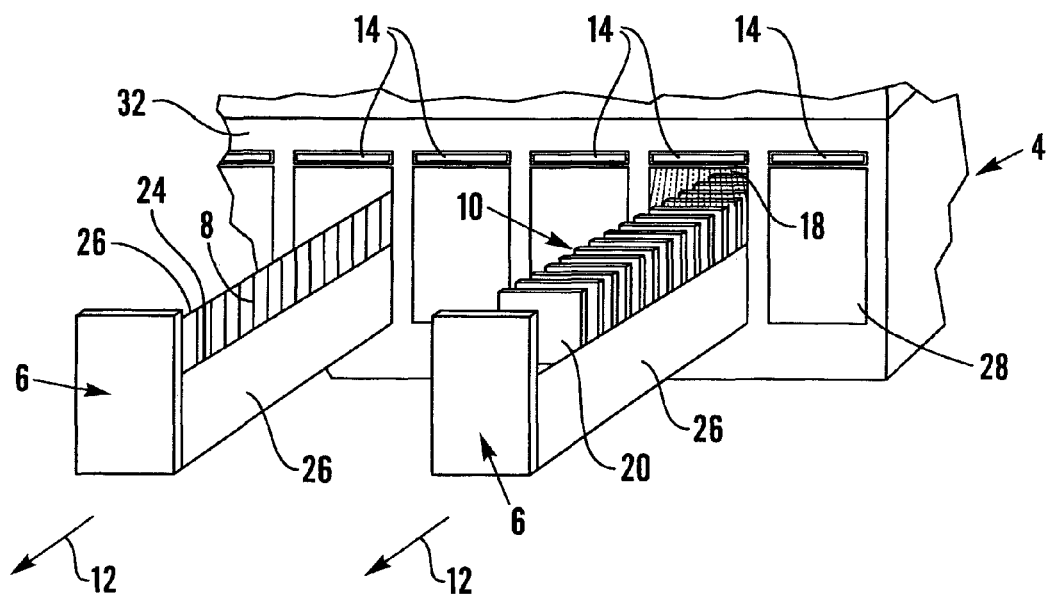
FIG. 1 shows a partial perspective view of a support structure of the archive apparatus according to the invention.
Figure 2:
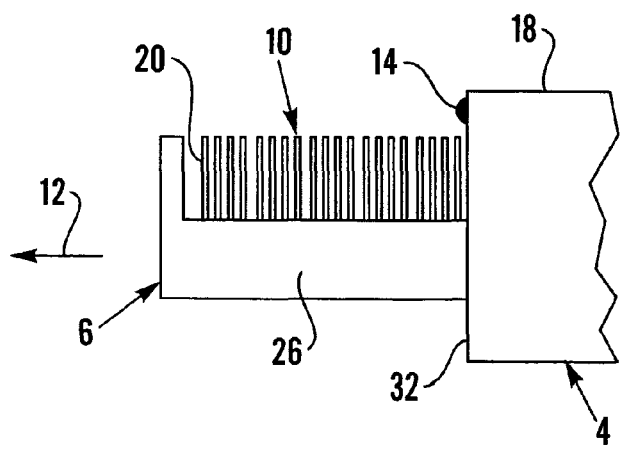
FIG. 2 shows a side view of a part of the support structure shown in FIG. 1 with a drawer pulled out.
Figure 3:
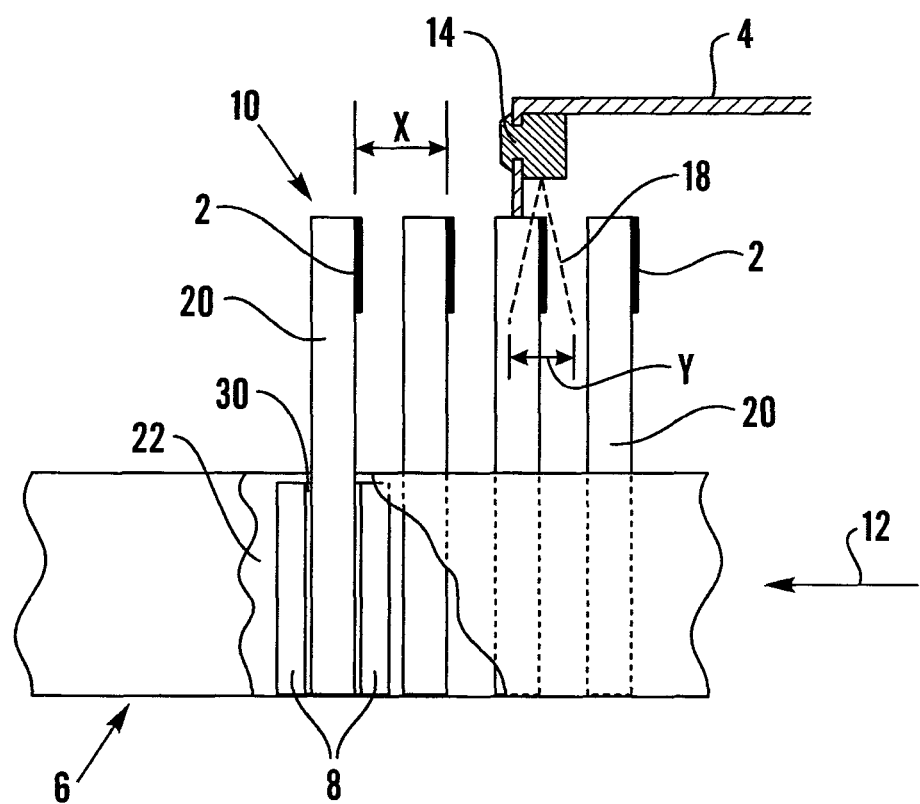
FIG. 3 shows a detailed partial side view, partly broken away, of the part of the support structure shown in FIG. 2.

Referring to FIG. 1 the support structure (hereinafter referred to as a cabinet 4) supports plural drawers 6 which are translatable in a translation direction 12 into and out of the cabinet 4. Although the term drawer has been used, there is no requirement for the drawer to even partly enclose a volume in which the slides are accommodated. It is merely necessary for it to be possible to draw the drawer at least partly out of the cabinet and for the drawer to support an array 10 of slides 20 by means of slide support means 8. The left hand drawer shown in FIG. 1 is empty and is pulled out of the cabinet 4 so as to show the slide support means which comprises vertical ribs 8 which project inwardly from inner surfaces 24 of confronting side walls 26 of the drawers 6. These ribs 8 are shown more clearly in the partially cut-away view of a drawer 6 shown in FIG. 3 and are spaced such that gaps 30 between them snugly accommodate a slide 20. The slides 20 are supported vertically with a relatively close pitch or centre spacing distance X as shown in FIG. 3. The distance X may conveniently be slightly more than the thickness of a slide.

As shown most clearly in FIG. 3, a radio frequency reader antenna 14 is mounted immediately above each drawer opening 28 in a front face 32 of the cabinet 4. Each reader antenna 14 is specially designed and configured to provide a curtain 18 of electromagnetic waves which can be used to power up the RFID tag 2 mounted on each slide 20. This may be achieved by the deployment of a shield close to the reader antenna with a slot formed therein to limit the extent to which electromagnetic waves emitted by the reader antenna spread out as they travel away from the reader antenna. With a slide mounted in the drawer with its RFID tag 2 positioned uppermost as show, where the curtain of electromagnetic waves 18 has a maximum dimension in the translation direction of a distance Y which is preferably less than the pitch X of the slides in order that the antenna reader will only read one RFID tag at any one time as the drawer is translated between its opened and closed positions.

Figure 4:
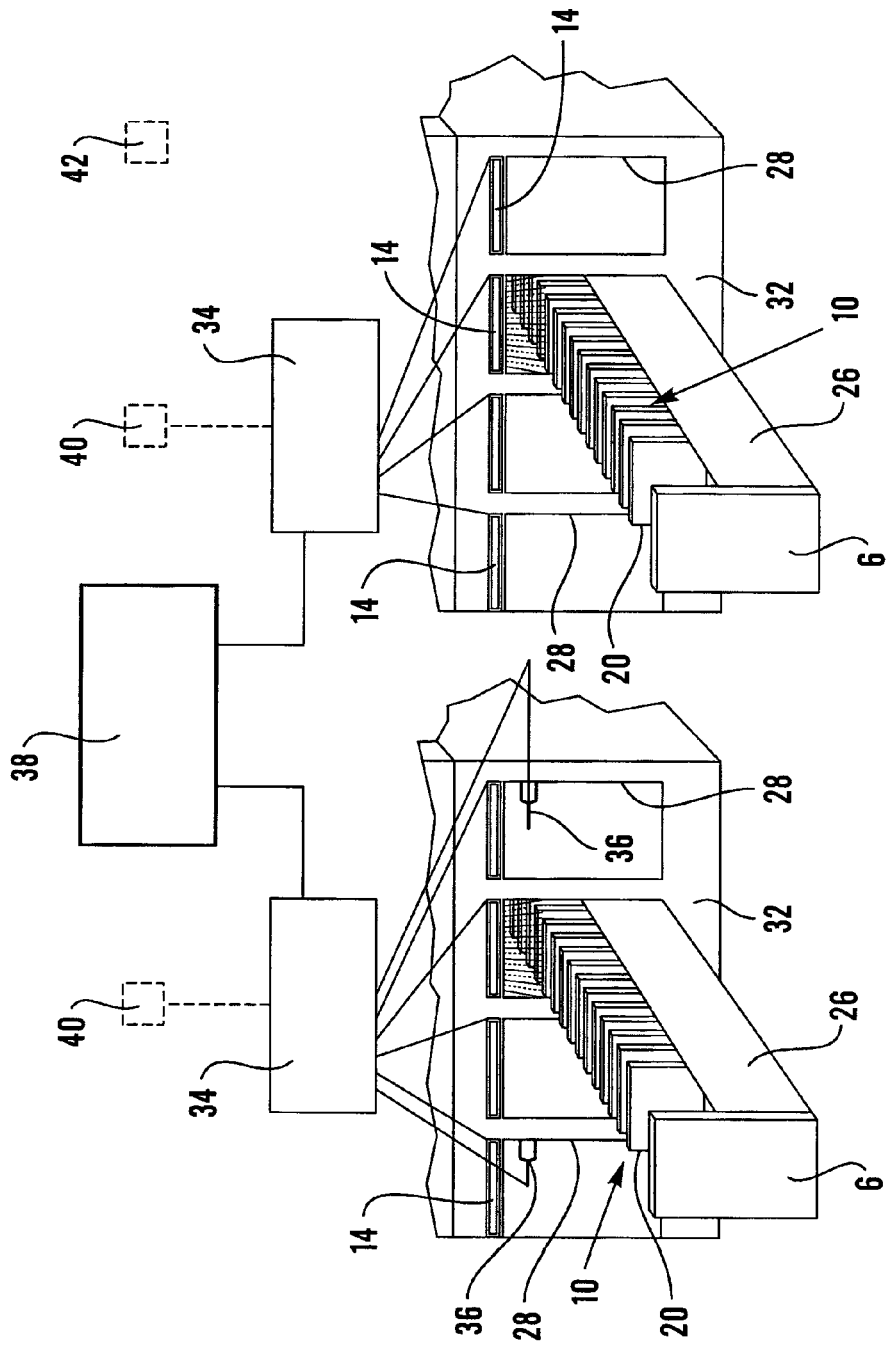
FIG. 4 shows the interconnections between plural support structures and associated controllers and a central computer.

As shown in FIG. 4, each reader antenna 14 is operatively connected, for example by a wire, to a controller. The connection may alternatively be by some non-wired means. The controller 34 may be provided with a signal from a drawer actuated switch (one only shown in FIG. 4) and actuate the appropriate reader antenna 14 upon sensing that a drawer opening activity has been commenced. Preferably a single controller 34 is mounted in each cabinet and controls the actuation of all of the reader antennae in that cabinet. The controller 34 may alternatively be connected to, rather than mounted within, the cabinet 4.

As a drawer 6 is progressively opened the reader antenna 14 over that drawer reads the RFID tag of each slide as it passes through the curtain 18 of electromagnetic radiation emitted by the reader antenna 14. Information from the RFID tag is routed by the controller 34 to a central computer 38 in which tracking software logs the information. When required this information can be supplied by the central computer and may be supplied in a graphic and/or text format which makes it readily apparent which slides are accommodated in each drawer and in what position in the drawer the slide is located. A graphical view of the physical storage units and their contents may be displayed. The controller may alternatively store the relevant information locally and not be connected to a central computer. In this case the controller would be interrogatable so as to provide information concerning the slides in the cabinet and also possibly historic information concerning slides in the cabinet.

The controller 34 may be configured to maintain an actuated reader antenna 14 in an active state until the associated drawer is closed as sensed by the associated switch 36 or for a certain period of time after actuation. The reader antenna 14 provides information to the central computer 38 via the controller 34 as the drawer is closed so that the tracking software can be updated to take account of any changes to the slides in the drawer by removal, addition or moving.

The support structure or cabinet 4 may also be provided with a reader 40 suitable for reading an identification badge 42 or other identification means of a user. Information relating to the user may be stored by the controller 34 and/or central computer 38 together with information concerning the samples 20 added to or removed from a particular drawer 6. The support structure could also be adapted to only unlock a particular support structure/drawer for a user who has been assigned appropriate authority. The user identification badge 42 could include information concerning such authority.

Various modifications to the apparatus and method, which would be obvious to a skilled person in the art, may be made without departing from the scope of the invention as defined in the following claims.

The invention claimed is:

1. Archive apparatus for storing and archiving laboratory samples including a radio frequency identifier, the apparatus comprising a support structure, a drawer translatable in a translation direction into and out of the support structure, a sample support associated with the drawer for supporting an array of samples spaced at a pitch along the translation direction for movement with the drawer, a radio frequency reader antenna connected to the support structure adjacent to the drawer wherein the reader antenna is configured to emit a curtain of electromagnetic waves, a shield deployed adjacent to the reader antenna with a slot formed therein to limit the extent to which emitted electromagnetic waves spread as the electromagnetic waves travel away from the reader antenna, the curtain of electromagnetic waves having a maximum dimension in the translation direction which is less than the pitch of the laboratory samples, and a recorder adapted to operatively communicate with the reader antenna to store information obtained from the radio frequency identifier of laboratory samples supported by the drawer.

2. The apparatus according to claim 1, wherein the recorder includes a controller operatively connected to the reader antenna.

3. The apparatus according to claim 2, wherein the controller is operatively connected to a computer system including sample tracking software.

4. The apparatus according to claim 1, wherein the support structure accommodates plural drawers.

5. The apparatus according to claim 4, wherein one said reader antenna is connected to the support structure adjacent to each drawer.

6. The apparatus according to claim 2, wherein the controller is operatively connected to plural said reader antennae.

7. A compound archive apparatus comprising plural archive apparatuses according to claim 1.

8. The compound archive apparatus according to claim 7, wherein the recorder includes a single computer system operatively connected to the reader antennae.

9. A method for storing and archiving laboratory samples with a radio frequency identifier including providing apparatus comprising a support structure, a drawer translatable in a translation direction into and out of the support structure, supporting the laboratory samples in an array in a sample support associated with the drawer with the laboratory samples spaced at a pitch along the translation direction for movement with the drawer, providing a radio frequency reader antenna connected to the support structure adjacent to the drawer and recorder and a shield deployed adjacent to the reader antenna with a slot formed therein to limit the extent to which emitted electromagnetic waves spread as the electromagnetic waves travel away from the reader antenna, translating the drawer in the translation direction so that the laboratory samples pass through a curtain of electromagnetic waves emitted by the reader antenna wherein the curtain has a maximum dimension in the translation direction which is less than the pitch of the laboratory samples, operatively communicating information from the radio frequency identifier (2) of the samples (20) supported by the drawer (6) to the recorder (34, 38) and recording said information with the recorder (34, 38).

10. The method according to claim 9, comprising the further steps of at least partly translating the drawer out of the support structure, altering a distribution of the samples supported by the drawer, translating the drawer back into the support structure and updating a record held by the recorder of samples supported by the drawer based on signals received by the reader antenna.

11. The method according to claim 9, wherein the recorder records historic information concerning the samples in the drawer in addition to current information concerning the samples in the drawer.

12. The method according to claim 9, wherein the stored information concerning samples supported by the drawer is displayed by the recorder graphically.

13. The method according to claim 9, including identifying a user accessing the samples by means of user identifier and using this identification to record which user has accessed the samples or to control access to the samples.

* * * * *